United States Patent
Igarashi et al.

(10) Patent No.: US 11,921,241 B2
(45) Date of Patent: Mar. 5, 2024

(54) ULTRASONIC PROBE AND ULTRASONIC DIAGNOSTIC APPARATUS USING THEREON

(71) Applicant: Hitachi, Ltd., Tokyo (JP)

(72) Inventors: Yutaka Igarashi, Tokyo (JP); Shinya Kajiyama, Tokyo (JP); Kengo Imagawa, Tokyo (JP)

(73) Assignee: FUJIFILM HEALTHCARE CORPORATION, Chiba (JP)

( * ) Notice: Subject to any disclaimer, the term of this patent is extended or adjusted under 35 U.S.C. 154(b) by 244 days.

(21) Appl. No.: 17/184,730

(22) Filed: Feb. 25, 2021

(65) Prior Publication Data

US 2021/0362187 A1 Nov. 25, 2021

(30) Foreign Application Priority Data

May 25, 2020 (JP) .................. 2020-090443

(51) Int. Cl.
*G01S 7/52* (2006.01)
*G01S 15/89* (2006.01)

(52) U.S. Cl.
CPC ...... *G01S 7/52033* (2013.01); *G01S 7/52046* (2013.01); *G01S 15/8925* (2013.01); *G01S 7/5208* (2013.01)

(58) Field of Classification Search
CPC ............. G01S 7/52033; G01S 7/52046; G01S 15/8925; G01S 7/5208
See application file for complete search history.

(56) References Cited

U.S. PATENT DOCUMENTS

| | | |
|---|---|---|
| 4,852,576 A | 8/1989 | Inbar et al. |
| 5,963,094 A | 10/1999 | Linder et al. |
| 7,365,600 B1 * | 4/2008 | Lokere .................. H03F 3/4595 330/258 |

(Continued)

FOREIGN PATENT DOCUMENTS

| | | | |
|---|---|---|---|
| CN | 104467770 A | * 3/2015 | ........... A61B 8/4444 |
| JP | 8-45460 A | 2/1996 | |

(Continued)

OTHER PUBLICATIONS

Japanese Office Action received in corresponding Japanese Application No. 2020-090443 dated Dec. 12, 2023.

*Primary Examiner* — Isam A Alsomiri
*Assistant Examiner* — Abdallah Abulaban
(74) *Attorney, Agent, or Firm* — Mattingly & Malur, PC

(57) ABSTRACT

An ultrasonic probe including: a plurality of transducers; a plurality of low-noise amplifier circuits individually corresponding to the plurality of transducers, the plurality of low-noise amplifier circuits having a variable resistor feedback unit making a resistance value variable by an electrical signal inputted to a control terminal; and a control circuit; wherein the control circuit has a dummy circuit generating a bias voltage of a feedback unit of the low-noise amplifier circuit, and an adding circuit outputting an added signal of a bias voltage by the dummy circuit and a control signal increasing or decreasing with a lapse of time; and the plurality of low-noise amplifier circuits input an output of the adding circuit to the control terminal of the variable resistor feedback unit to perform variable control on a gain of the low-noise amplifier circuit.

13 Claims, 5 Drawing Sheets

(56) References Cited

U.S. PATENT DOCUMENTS

| | | | | |
|---|---|---|---|---|
| 8,226,563 B2* | 7/2012 | Peteresen | ............. | G01S 7/5208 |
| | | | | 600/443 |
| 8,847,685 B2 | 9/2014 | Naeini et al. | | |
| 2009/0105587 A1* | 4/2009 | Petersen | ............... | G01S 7/5208 |
| | | | | 600/437 |

FOREIGN PATENT DOCUMENTS

| | | | |
|---|---|---|---|
| JP | 2004008684 A | * | 1/2004 |
| JP | 2012-244448 A | | 12/2012 |
| JP | 2013-188421 A | | 9/2013 |
| JP | 2016163608 A | * | 9/2016 |
| WO | 2012/139665 A1 | | 10/2012 |

* cited by examiner

ULTRASONIC PROBE AND ULTRASONIC DIAGNOSTIC APPARATUS USING THEREON

CROSS-REFERENCE TO RELATED APPLICATION

The present application claims priority from Japanese application JP 2020-090443, filed on May 25, 2020, the contents of which is hereby incorporated by reference into this application.

BACKGROUND OF THE INVENTION

The present invention relates to an ultrasonic probe and an ultrasonic diagnostic apparatus using thereon.

A two-dimensional (2D) array ultrasonic probe intended for an ultrasonic diagnostic apparatus is composed of a 2D array transducer having transducers two-dimensionally disposed and a 2D array integrated circuit (IC) driving the 2D array transducer. The 2D array ultrasonic probe has to include the 2D array IC that allows transmission and reception to and from about 200 signal terminals for an array of a few thousands to ten thousand transducers. The 2D array IC controls the timing of driving the transducers and operates the transmission and reception directions of ultrasonic beams.

The individual transducers of the 2D array transducer are connected to transmitting circuit-receiver circuits (in the following, referred to as element channel (ECh) circuits) one on one. A sub channel (in the following, a sub channel (SCh)) bundling N ECh circuits is connected to a transmission and reception signal input-output cable one to one. The meaning "beamform" will be described later.

In order to focus ultrasonic beams transmitted and received from the individual transducers of the 2D array transducer on a diagnostic organ inside a given living body, when it is assumed that the velocities of ultrasonic waves in the living body are equal, the ECh circuit has to allocate delay time proportions to the distances from the focal point to the individual transducers of the 2D array transducer. The ECh circuit allocates a larger delay to a transducer closer to the focal point, and allocates a smaller delay time to a farther transducer.

In reception, the output signals of all the ECh circuits in one SCh are added. This is referred to as phasing addition. The added signal is outputted from the cable to the ultrasonic diagnostic apparatus. In transmission, a signal transmitted from the ultrasonic diagnostic apparatus is branched to all the ECh circuits in one SCh, the signal is allocated with a delay at the ECh circuits, and the signal is outputted from each of the transducers. This is the meaning of "beamform".

The resolution of an ultrasonic tomogram image created by processing signals received from the 2D array ultrasonic probe depends on the dimensions of one transducer, and dimensions ranging from 200 to 300 µm, for example, is demanded. The resolution also depends on the delay time resolution that the delay circuit of the ECh circuit can set. The viewing angle of the ultrasonic tomogram image depends on the maximum delay time that the delay circuit of the ECh circuit can set.

Since the 2D array ultrasonic probe is a system that transmits ultrasonic waves by itself and receives the reflected waves, the 2D array ultrasonic probe is affected by a strong sound pressure reflected from bones, for example, in image acquisition of a site close to the body surface. When a level is designed such that the reception system of the 2D array IC, specifically a first stage noise amplifier circuit (in the following, also referred to as a low-noise amplifier (LNA)) is not saturated even at a strong sound pressure, and a gain is small, and noise characteristics deteriorate, resulting in the degradation in the signal-to-noise ratio SNR of images of deep sites. Therefore, in a typical ultrasonic diagnostic apparatus, which is not the 2D array ultrasonic probe, a system is used in which gain is increased corresponding to a lapse of time from the start of reception, and this is referred to as time gain control (in the following, also written as "TGC").

As the background techniques of implementation of TGC circuits, there are Japanese Unexamined Patent Application Publication No. 2013-188421 and U.S. Pat. No. 8,226,563.

An ultrasonic diagnostic apparatus described in Japanese Unexamined Patent Application Publication No. 2013-188421 includes a transmitting unit configured to transmit a transmission signal as an ultrasound signal through an ultrasound probe to an examinee, and a receiving unit configured to process an obtained reception signal reflected off inside the examinee. The receiving unit includes a transmission-reception switching unit configured to prevent a sneak path of the transmission signal to the receiving unit for separating transmission from reception, an amplifying unit configured to amplify the reception signal, and an attenuating unit disposed between the transmission-reception switching unit and the amplifying unit, the attenuating unit being configured to attenuate the reception signal. The attenuating unit changes the amount of attenuation from a large amount to a small amount such that a reflection signal from a short range, in which a signal with a large amplitude, is attenuated immediately after the end of transmission and a signal from a long range, in which signal amplitude is small, is not attenuated (see Abstract).

U.S. Pat. No. 8,226,563 discloses that in a receiver circuit for ultrasound images, the bias current of a preamplifier 14 connected to transducer elements 12 is changed, or the amount of feedback of a differential output amplifier 22 provided in the subsequent stage of the preamplifier 14 is adjusted, and thus the gain of the amplifier is can be varied (see FIGS. 3 and 4).

SUMMARY OF THE INVENTION

Although the ultrasonic diagnostic apparatus described in Japanese Unexamined Patent Application Publication No. 2013-188421 has the attenuating unit in the previous stage of the amplifying unit, an external circuit generates and inputs control signals. Since a diode is used, there is a problem that a variation in the degree of attenuation of the variable attenuator is large.

The ultrasonic diagnostic apparatus described in U.S. Pat. No. 8,226,563 performs TGC using the preamplifier, makes the bias current variable, provides a current feedback type using a MOSFET in a resistor, and hence achieves the gain varying function. However, in varying the bias current, the variable range of the gain is small, and a problem is grown in which distortion is increased when the current value is small. In the case where the current feedback type is provided using the MOSFET for the resistor, there is a problem that the gain greatly depends on processing.

The TGC circuit installed on the 2D array ultrasonic probe is necessary to have an LNA with an independent gain varying function for an array of each of a few thousands to ten thousand transducers. In the configurations described in Japanese Unexamined Patent Application Publication No. 2013-188421 and U.S. Pat. No. 8,226,563, it is difficult to minimize a variation in the gains of the LNAs while a gain varying function (30 dB or more) necessary to a few thousands to ten thousand LNAs. Consequently, these configurations fail to achieve configurations in which gain control signals are supplied to a large number of LNA groups disposed in a 2D array shape (a matrix configuration) for TGC control without increasing the areas of the LNAs.

An object of the present invention is to provide an ultrasonic probe that solves the problems above and achieves a TGC circuit suited to installation on a 2D array ultrasonic probe and an ultrasonic diagnostic apparatus using thereon.

An example of "an ultrasonic probe" according to an aspect of the present invention in order to solve the problem is an ultrasonic probe transmitting an ultrasonic wave to a diagnostic organ and receiving a reception signal that is a reflected wave. The ultrasonic probe includes: a plurality of transducers; a plurality of low-noise amplifier circuits individually corresponding to the plurality of transducers and having a variable resistor feedback unit making a resistance value variable by an electrical signal inputted to a control terminal; and a control circuit. The control circuit has a dummy circuit generating a bias voltage of a feedback unit of the low-noise amplifier circuit, and an adding circuit outputting an added signal of a bias voltage by the dummy circuit and a control signal increasing or decreasing with a lapse of time; and the plurality of low-noise amplifier circuits input an output of the adding circuit to the control terminal of the variable resistor feedback unit to perform variable control on a gain of the low-noise amplifier circuit.

According to the present invention, an ultrasonic probe that achieves a TGC circuit suited to installation on a 2D array ultrasonic probe and an ultrasonic diagnostic apparatus using thereon can be provided.

Objects, configurations, and effects other than ones described above will be apparent from the description of embodiments below.

DETAILED DESCRIPTION OF THE PREFERRED EMBODIMENTS

Figure 1:
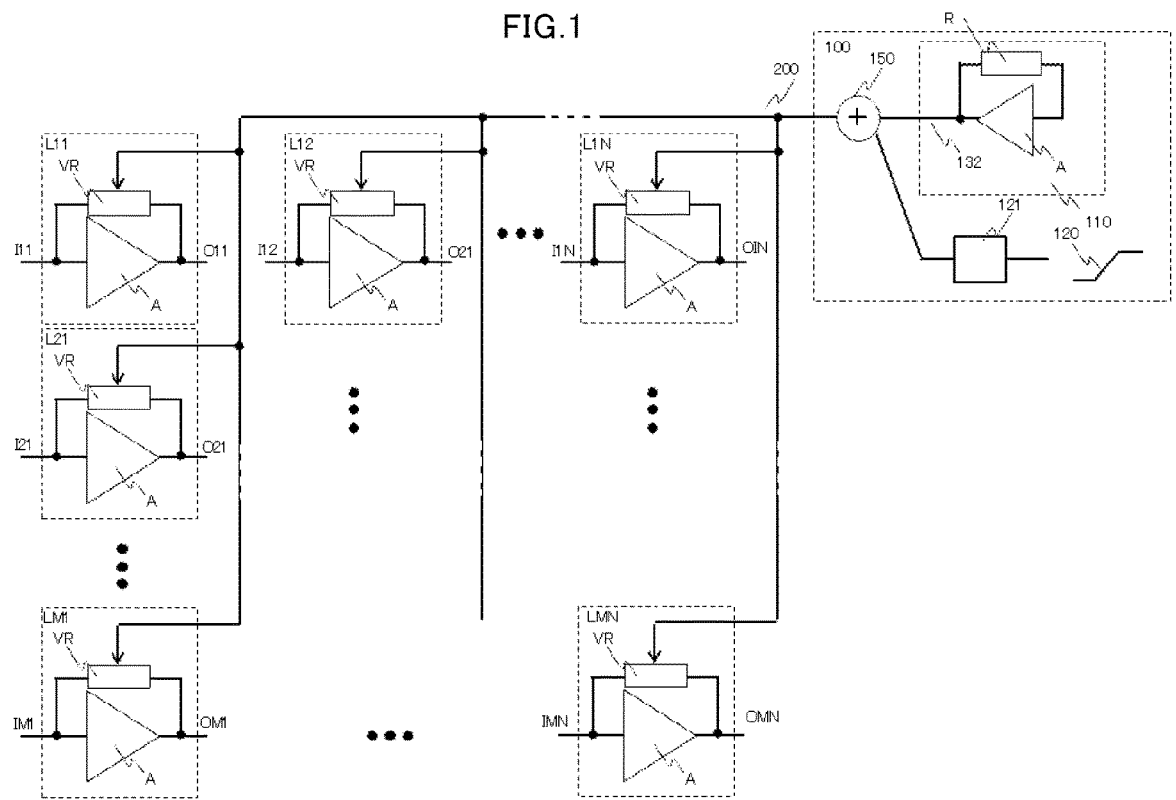
FIG. 1 is a block diagram of LNAs and components around the LNAs according to a first embodiment.

In the following, embodiments according to the present invention will be described with reference to the drawings. Note that in the drawings for explaining the embodiments, the same components are designated with the same names and the same reference signs, and the duplicate description is omitted.

Notations such as "first", "second", and "third" in the present specification are given in order to identify components, and these notations do not necessarily limit numbers or orders. The numbers for identifying components in each context, and a number used in one context does not necessarily indicate the same configuration in another context. A component identified by a certain number does not preclude the identified component from combining the function of a component identified by another number.

First Embodiment

FIG. 1 is a block diagram of LNAs and components around the LNAs according to a first embodiment, which configures a TGC circuit. In FIG. 1, reference signs L11 to LMN indicate low-noise amplifier circuit LNAs. In the LNA, A is an amplifier circuit, and VR is a variable resistor. A reference sign 100 indicates a TGC control circuit that is composed of a dummy circuit 110 for the LNA, the dummy circuit 110 outputting a replica signal 132, a signal slope inverting circuit 121 receiving a TGC control signal 120 and outputting an inverted signal, and an adding circuit 150. The TGC control circuit 100 outputs a variable resistor control signal 200.

M×N LNAs (L11 to LMN) are circuits designed with the same circuit constants, and are circuits to which negative feedback is applied to the amplifier circuit A by the variable resistor VR. Since the LNAs are mounted on the same semiconductor die, variation in characteristics of the LNAs is sufficiently small. The gain of the LNA is determined by the element value of the VR connected in order to apply negative feedback when the gain of the amplifier circuit A is sufficiently large. The signals inputted to input terminals I11 to IMN are amplified by the gain, and the amplified signals are outputted from respective output terminals O11 to OMN. The variable resistor VR varies the resistance value by the voltage inputted to an arrow terminal. At this time, no electric current is assumed to be inputted to or outputted from the arrow terminal. The voltage inputted to the arrow terminal is varied and the value of the VR is varied, the gain of the LNA is determined by the element value of the VR, and thus the gain can be varied. When the resistance value of the VR is small, the gain of the LNA is low, whereas when the resistance value of the VR is large, the gain of the LNA is large.

The TGC control signal 120 is a signal increasing with a lapse of time. The TGC control signal 120 is generated at a TGC control signal generation circuit described later in a sixth embodiment. The TGC control signal generation circuit may be built-in the ultrasonic probe, or the TGC control signal may be supplied externally from the outside of the ultrasonic probe using a cable.

When an increase in the voltage to be inputted to the arrow terminal of the VR in the LNA causes an increase in the resistance value, the signal slope inverting circuit 121 outputs the TGC control signal 120 as the same slope polarity. Conversely, when a decrease in the voltage to be inputted to the arrow terminal of the VR causes an increase in the resistance value, the signal slope inverting circuit 121 converts the TGC control signal 120 into "a signal decreasing with a lapse of time", which has a polarity reverse to that of the TGC control signal 120, and outputs the converted signal.

The dummy circuit 110 of the LNA is composed of the amplifier circuit A and a resistor R, and outputs a replica signal 132 of the bias voltage of the variable resistor VR connected to the feedback unit of the LNA. Similarly to the LNA, the variable resistor VR may be used in order to obtain the replica signal 132. However, since the dummy circuit does not need the function of amplifying signals, in FIG. 1, a typical resistor R with no need of the arrow terminal, and a circuit applied with negative feedback is provided. The dummy circuit 110 is mounted on the same semiconductor die on which a plurality of the LNAs are mounted. The difference between the voltage of the arrow terminal of the variable resistor VR and the bias voltage of the variable resistor VR determines the resistance value of the variable resistor VR. When the bias voltage of the variable resistor VR is VRB and the voltage of the arrow terminal is VRC, the resistance value RVR of the variable resistor VR is RVR ∝1/(VRC−VRB). Since the VRB fluctuates depending on the conditions including variation in processes of a semiconductor from which the LNA is manufactured, power supply voltages, and ambient temperatures, the RVR also fluctuate corresponding to the conditions. For this reason, the replica signal 132 of the bias voltage of the variable resistor VR is generated from the dummy circuit for the LNA, and the variable resistor control signal 200, which the output of the signal slope inverting circuit 121 is added to the replica signal 132, is supplied to the arrow terminal of the variable resistor VR. Thus, even though the VRB fluctuates due to the reason above, the replica signal 132 also fluctuate corresponding to the fluctuation, and hence the RVR is a fixed value. This enables the LNA to perform operation with gain characteristics having small variation, the gain characteristics increasing with a lapse of time necessary in TGC. Since no electric current is inputted to or outputted from the arrow terminal of the variable resistor VR, one variable resistor control signal 200 can be supplied to the arrow terminals of the variable resistors VR in M×N LNAs (L11 to LMN) with no consumption of electric power, and thus all the LNAs are enabled to perform the same operation.

Although M×N LNAs are mounted in a matrix configuration on the same semiconductor die, one TGC control circuit can be disposed around the semiconductor die at a high degree of freedom, and thus an increase in the circuit size can be suppressed.

According to the present embodiment, an LNA can be achieved, the LNA having a gain varying function with a small variation independently and individually on an array of a few thousands to ten thousand transducers. Time gain control is enabled with a large number of the LNAs disposed in a 2D array configuration, while the circuit size and power consumption are reduced, and thus an ultrasonic diagnostic apparatus including a 2D array ultrasonic probe improving the SNR of diagnostic images of both near and deep sites can be provided.

Second Embodiment

Figure 2:
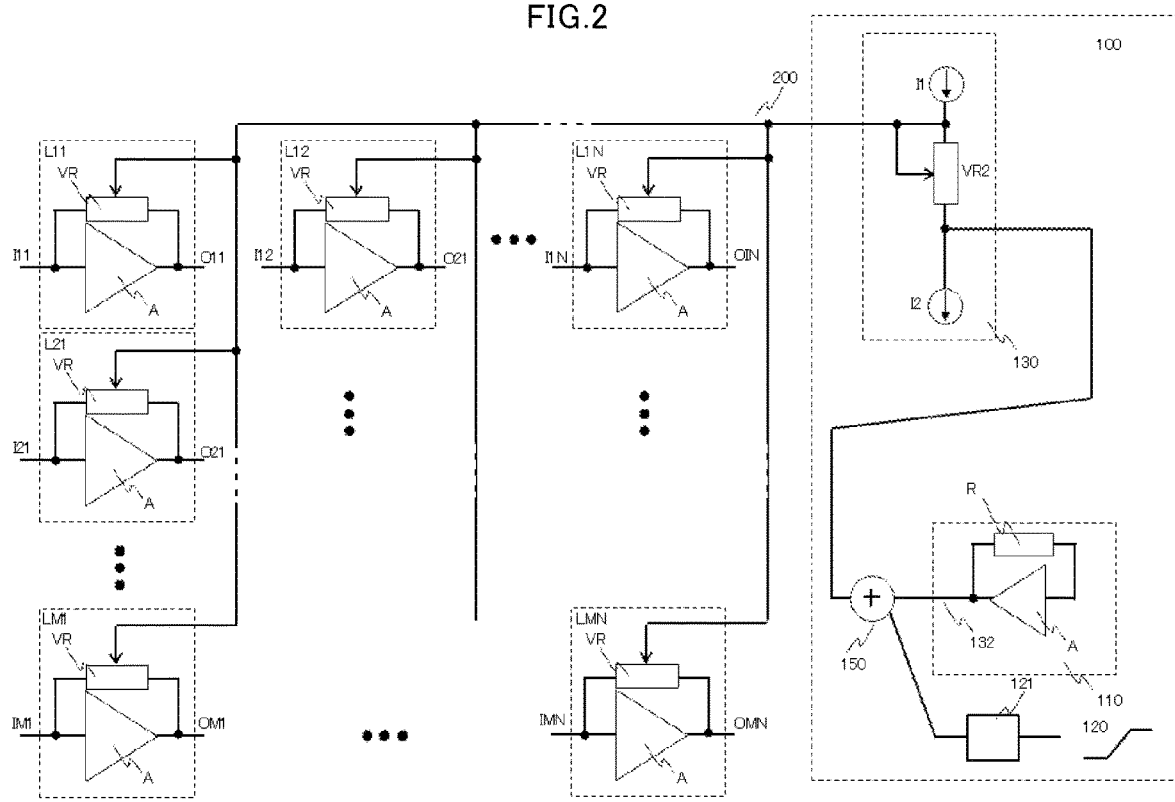
FIG. 2 is a block diagram of LNAs and components around the LNAs according to a second embodiment.

FIG. 2 is a block diagram of LNAs and components around the LNAs according to a second embodiment, which constitute a TGC circuit. In FIG. 2, components the same as the components in FIG. 1 are designated with the same reference signs as those in FIG. 1, and the description is omitted.

In FIG. 2, a reference sign 130 denotes a floating voltage circuit. Here, a variable resistor VR of an LNA will be described that an increase in a voltage to be inputted to an arrow terminal decreases a resistance value. In the first embodiment, the description is made that the resistance value RVR of the variable resistor VR is determined by the difference between the voltage signal of the arrow terminal and the bias voltage. However, some variable resistors VR have variation depending on their semiconductor manufacture processes. When a variable to be changed by a manufacture process is VRP, the variable can be expressed by RVR ∝1/(VRC−VRB−VRP). In the case of using such a variable resistor, in the configuration in the first embodiment, even though RVR is not changed to VRC−VRB, VRP changes RVR, resulting in the occurrence of an error in the gain of the LNA. In order to correct this error, the floating voltage circuit 130 is provided in a TGC control circuit 100. The floating voltage circuit 130 uses a variable resistor VR2 using the same element as the variable resistor VR, and constant current sources I1 and I2 are provided above and below the variable resistor VR2. At the arrow terminal of the variable resistor VR2, "an increase in the voltage decreases the resistance value", and connection is made to the terminal with a high potential in the variable resistor VR2 other than the arrow terminal. When connection is made to the terminal with a low potential, the resistance value becomes too large. When an electric current is carried from the constant current sources I1 and I2, the voltage across the terminals of the variable resistor VR2 becomes too large to operate. The current values of the constant current sources I1 and I2 are set to the same. At this time, a voltage, in which the level shift of the voltage across the terminals of the variable resistor VR2 is added to the output of an adding circuit 150, is a variable resistor control signal 200. With this configuration, the RVR is increased when the VRP is large due to the manufacture process. However, the voltage across the terminals of the variable resistor VR2 is also increased, and thus the influence of the VRP is corrected. Accordingly, even though the VRB or the VRP fluctuates due to the reasons above, the TGC control circuit 100 outputs the variable resistor control signal 200 that fluctuates correspondingly, the RVR is a fixed value, and thus this enables the LNA to perform operation with gain characteristics having small variation, the gain characteristics increasing with a lapse of time necessary in TGC. Since no electric current is assumed to be inputted to or outputted from the arrow terminal of the VR, one variable resistor control signal 200 can be supplied to the arrow terminals of the variable resistors VR in M×N LNAs (L11 to LMN) with no consumption of electric power, and thus all the LNAs are enabled to perform the same operation.

According to the present embodiment, in addition to the effect of the first embodiment, an ultrasonic diagnostic apparatus that corrects variation depending on the semiconductor manufacture process of the variable resistor VR can be provided.

Third Embodiment

Figure 3:
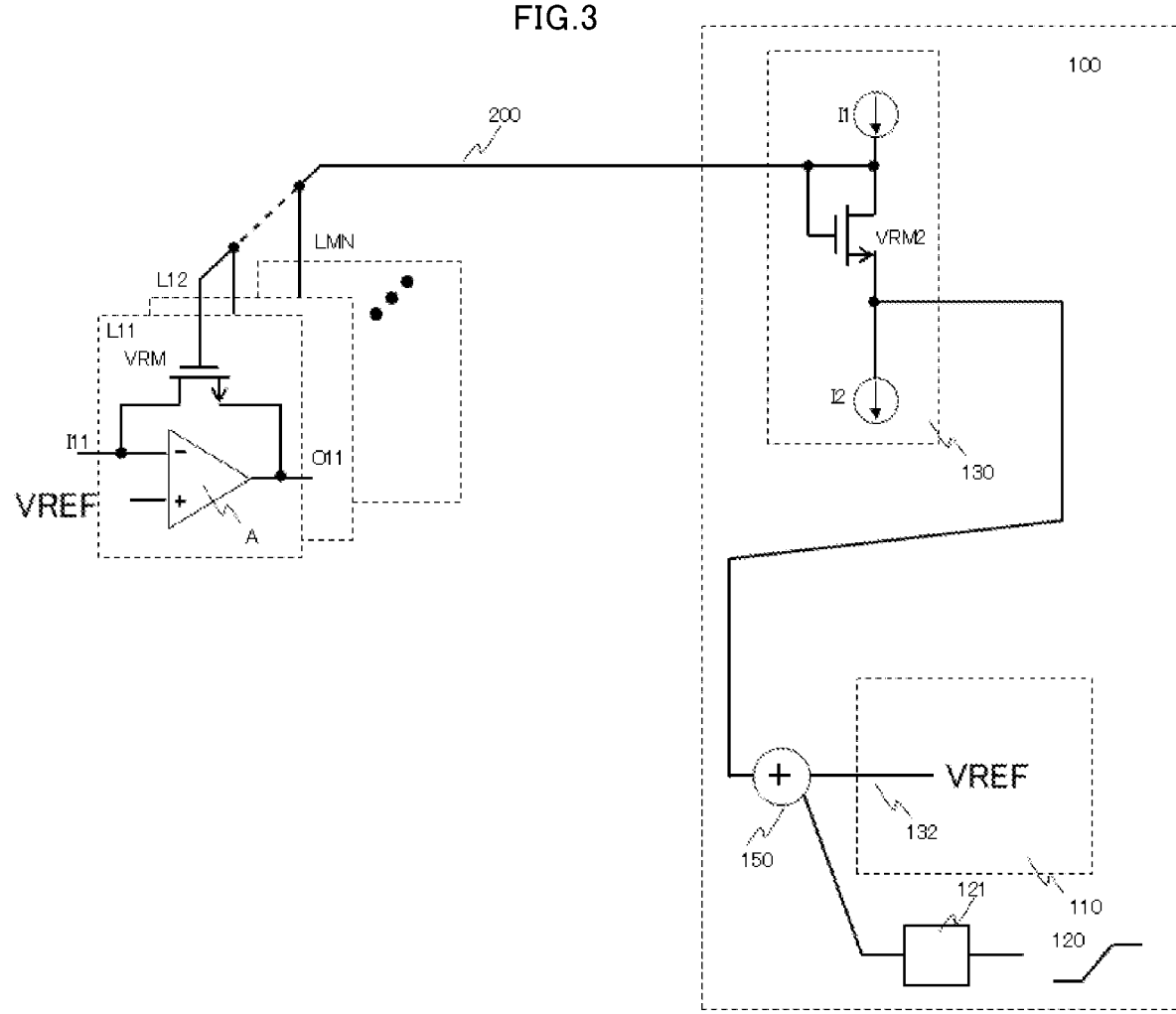
FIG. 3 is a block diagram of LNAs and components around the LNAs according to a third embodiment.

FIG. 3 is a block diagram of LNAs and components around the LNAs according to a third embodiment, which constitute a TGC circuit. In FIG. 3, components the same as the components in FIGS. 1 to 2 are designated with the same reference signs as those in FIGS. 1 and 2 and the description is omitted. However, for simplification, only L11 is shown, and others are depicted by stacked rectangular broken lines.

In FIG. 3, reference signs VRM and VRM2 denote N-channel field effect transistors and a reference sign VREF denotes a reference voltage. In LNAs (L11 to LMN), an operational amplifier (OP amplifier) is used as the amplifier circuit A, and the N-channel field effect transistor VRM is used as the variable resistor VR that applies negative feedback from the output of the operational amplifier to the inverting input terminal. This circuit outputs a voltage signal that is an RVR-times current signal input. The potentials of the non-inverting input terminal and the inverting input terminal are equal. Therefore, when the current signal input is zero, no electric current is carried through the VRM, and the VRM is biased to the reference voltage VREF.

As the variable resistor VR2, the N-channel field effect transistor VRM2 having a diode connected is used. In the case of this LNA, the bias voltage of the VRM is the reference voltage VREF itself, and thus a dummy circuit 110 for the LNA can use the reference voltage VREF as a replica signal 132 only with the supply of the reference voltage VREF.

The terminal of the LNA corresponding to the arrow terminal of the variable resistor VR in FIGS. 1 and 2 is the gate of the VRM, no electric current is inputted or outputted, and thus one variable resistor control signal 200 can be supplied to M×N LNAs (L11 to LMN) with no consumption of electric power. Accordingly, all the LNAs are enabled to perform the same operation.

According to the present embodiment, the effect of the second embodiment can be exerted with no provision of the dummy circuit.

Fourth Embodiment

Figure 4:
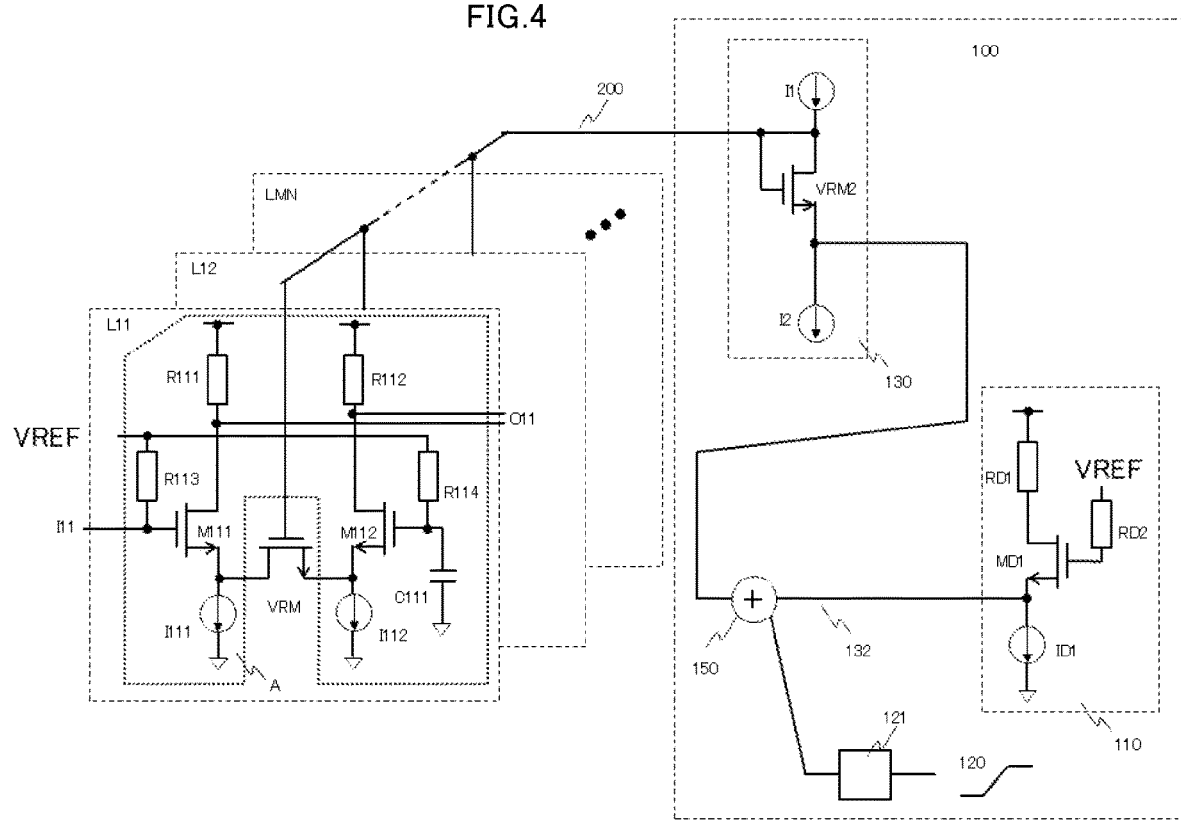
FIG. 4 a block diagram of LNAs and components around the LNAs according to a fourth embodiment.

FIG. 4 is a block diagram of LNAs and components around the LNAs according to a fourth embodiment, which constitute a TGC circuit. In FIG. 4, components the same as the components in FIGS. 1 to 2 are designated with the same reference signs as those in FIGS. 1 and 2 and the description is omitted. However, for simplification, only the LNA (L11) is shown, and others are depicted by stacked rectangular broken lines.

In FIG. 4, Rxxx and RDxxx denote resistors, Cxxx denotes a capacitance, Mxxx and MDxxx denote N-channel field effect transistors, and Ixxx and IDxxx denote electric current source. Here, xxx are numerical characters.

In LNAs (L11 to LMN), a differential amplifier circuit is used as the amplifier circuit A, and an N-channel field effect transistor VRM is used as the variable resistor VR. The N-channel field effect transistor VRM is connected between the sources of two N-channel field effect transistor M111 and M112 constituting the differential amplifier circuit. The differential amplifier circuit having a resistor element connected between the sources in this manner is referred to as source degeneration. This enables a decrease the gain and amplification of an input signal having a large amplitude with a low distortion as well. The LNAs (L11 to LMN) replace the resistor element between the sources by the field effect transistor VRM, and the gate voltage is changed to provide a function that varies the gain.

Although the differential amplifier circuit itself may be used as the dummy circuit 110 for the LNA, as shown in FIG. 4, the replica signal 132 can be generated also using its half circuit in which a resistor RD1, an N-channel field effect transistor MD1, and an electric current source ID1 are connected in series. At the gate of the N-channel field effect transistor MD1, the reference voltage VREF is applied through a resistor RD2.

The terminal of the LNA corresponding to the arrow terminal of the variable resistor VR in FIGS. 1 and 2 is the gate of the N-channel field effect transistor the VRM, no electric current is inputted or outputted, and thus one variable resistor control signal 200 can be supplied to M×N LNAs (L11 to LMN) with no consumption of electric power. Accordingly, all the LNAs are enabled to perform the same operation.

According to the present embodiment, an LNA can be achieved, the LNA having a gain varying function with a small variation independently and individually on an array of a few thousands to ten thousand transducers. TGC control is enabled with a large number of the LNAs disposed in a 2D array configuration, while the circuit size and power consumption are reduced, and thus an ultrasonic diagnostic apparatus including a 2D array ultrasonic probe improving the SNR of diagnostic images of both near and deep sites can be provided.

Fifth Embodiment

Figure 5:
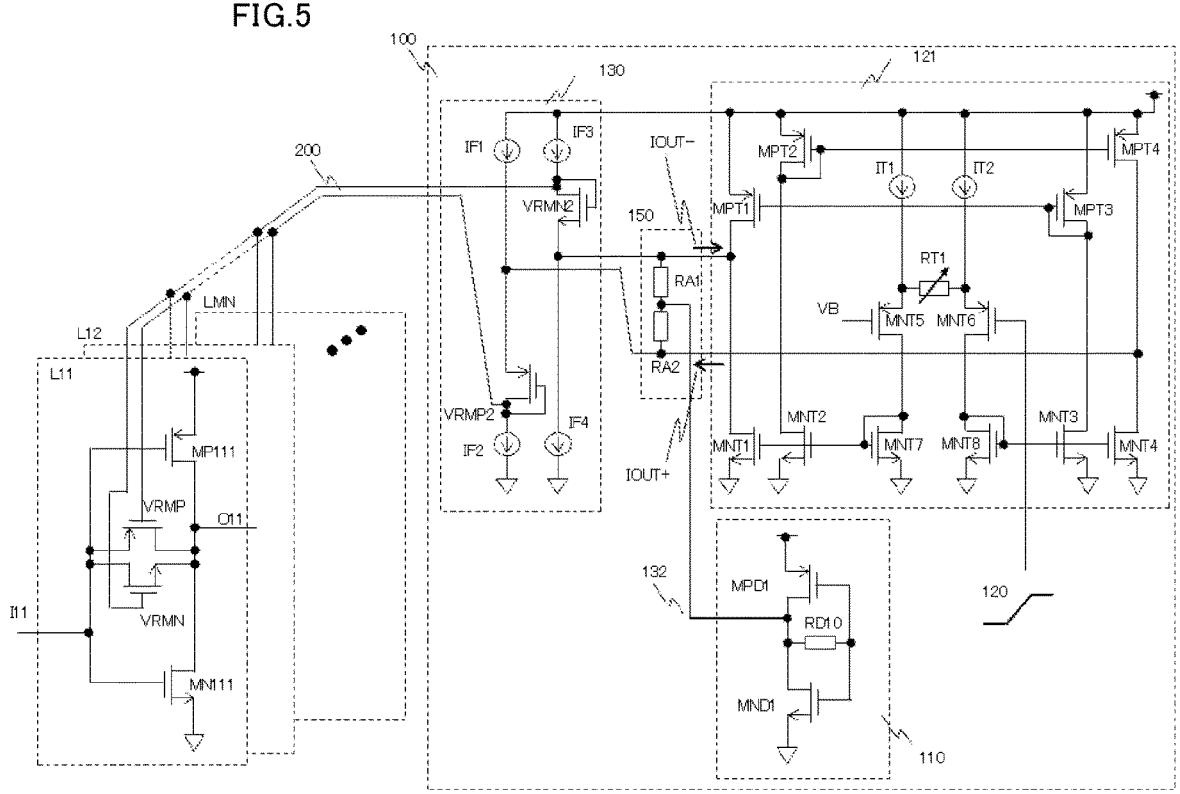
FIG. 5 a block diagram of LNAs and components around the LNAs according to a fifth embodiment.

FIG. 5 is a block diagram of LNAs and components around the LNAs according to a fifth embodiment, which constitute a TGC circuit. In FIG. 5, components the same as the components in FIGS. 1 to 2 are designated with the same reference signs as those in FIGS. 1 and 2 and the description is omitted. However, for simplification, only the LNA (L11) is shown, and others are depicted by stacked rectangular broken lines.

In FIG. 5, RTxxx denotes a variable resistor, RAxxx and RDxxx denote resistors, VRMN, VRMN2, MNxxx, MNDxxx, and MNTxxx denote N-channel field effect transistors, VRMP, VRMP2, MPxxx, MPDxxx, and MPTxxx denote P-channel field effect transistors, IFxxx and ITxxx denote electric current sources, and VB denotes a reference voltage. Here, xxx are numerical characters.

In LNAs (L11 to LMN), an amplifier circuit A uses a CMOS inverter circuit connecting the N-channel field effect transistor MNxxx to the P-channel field effect transistor MPxxx in series with a variable resistor VR in which the P-channel field effect transistor VRMP is connected to the N-channel field effect transistor VRMN in parallel. This is because, since an output terminal Oxx greatly fluctuates around a potential of approximately a power supply voltage×0.5 in the range of a power supply voltage or less when a signal is inputted to an input terminal Ixx, a constant feedback resistance value is to be achieved as much as possible even at a potential larger than or a potential smaller than a potential of a power supply voltage×0.5.

In the P-channel field effect transistor, the drain-source resistance value becomes large when the potential of the gate to the source becomes large, whereas the drain-source resistance value becomes small when the potential of the gate to the source becomes small. Conversely, in the N-channel field effect transistor, the drain-source resistance value becomes small when the potential of the gate to the source becomes large, whereas the drain-source resistance value becomes large when the potential of the gate to the source becomes small. That is, the slope of a TGC control signal 120 is changed at a signal slope inverting circuit 121, and the resistance value is increased with a lapse of time at both of the N-channel field effect transistor VRMN and the P-channel field effect transistor VRMP. This can be achieved by a single differential converter circuit composed of MNTxxx, MPTxxx, and ITxxx, the single differential converter circuit constituting the signal slope inverting circuit 121.

In the single differential converter circuit composed of the N-channel field effect transistor MNTxxx, the P-channel field effect transistor MPTxxx, and the electric current source ITxxx, the electric current sources IT1 and IT2 have the same current value, the N-channel field effect transistors MNT5 and MNT6, the N-channel field effect transistors MNT7 and MNT8, the N-channel field effect transistors MNT1 to MNT4, and the P-channel field effect transistors MPT1 to MPT4 are in the same size. In this circuit, when the TGC control signal 120 is increased, an electric current IOUT+ going out from the node of the MPT4 and the MNT4 and an electric current IOUT− coming in the node of the MPT1 and the MNT1 are increased. The IOUT+ and the IOUT− have the same value, and these values are inputted to the series connected circuit of the resistors RA1 and RA2 (having the same value as the RA1) in an adding circuit 150. To the node of the resistors RA1 and RA2 series connected in the adding circuit 150, a replica signal 132 is inputted. The TGC control signal 120 increased with a lapse of time causes operation in which the potential of the node of the MPT4 and the MNT4 is increased around the level of the replica signal 132 and the potential of the node of the MPT1 and the MNT1 is decreased. In other words, the operation of adding the replica signal 132 to the signal increased or decreased with a lapse of time can be achieved using a simple circuit composed of the resistors RA1 and RA2.

The variable resistor RT1 of the signal slope inverting circuit 121 can be varied, and the velocity at which the resistance value is increased with a lapse of time can be converted. When the reference voltage VB is made variable, the TGC control signal 120 and the timing of actually increasing the resistance value can be changed. That is, the gain of the single differential converter circuit is made variable, or the reference voltage is made variable, and thus the gain of the LNA can be varied.

To the output of the adding circuit 150, a floating voltage circuit 130 performs a level shift by the floating voltage corresponding to the N-channel field effect transistor VRMN and the P-channel field effect transistor VRMP, a pair of variable resistor control signals 200 is connected in series to the gate terminals of the N-channel field effect transistor VRMN and the P-channel field effect transistor VRMP of the LNAs (L11 to LMN).

The terminal of the LNA corresponding to the arrow terminal of the variable resistor VR in FIGS. 1 and 2 is the gates of the N-channel field effect transistor VRMN and the P-channel field effect transistor VRMP, no electric current is inputted or outputted, and thus the pair of variable resistor control signals 200 can be supplied to M×N LNAs (L11 to LMN) with no consumption of electric power. Accordingly, all the LNAs are enabled to perform the same operation.

According to the present embodiment, an LNA can be achieved, the LNA having a gain varying function with a small variation independently and individually on an array of a few thousands to ten thousand transducers. TGC control is enabled with a large number of the LNAs disposed in a 2D array configuration, while the circuit size and power consumption are reduced, and thus an ultrasonic diagnostic apparatus including a 2D array ultrasonic probe improving the SNR of diagnostic images of both near and deep sites can be provided.

Sixth Embodiment

Figure 6:
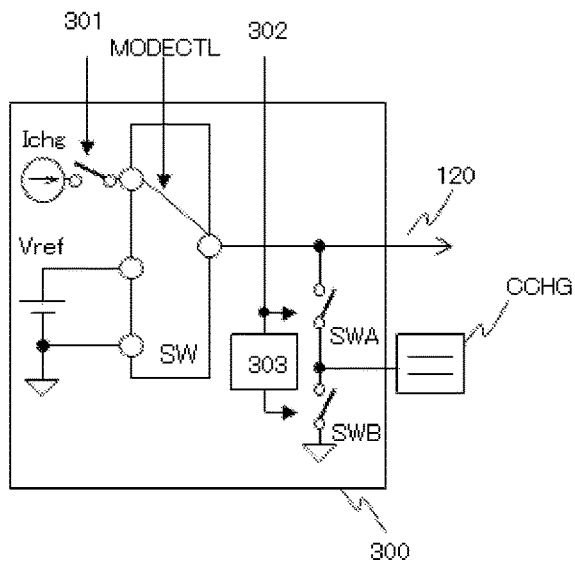
FIG. 6 is a block diagram of a TGC control signal generation circuit according to a sixth embodiment.

FIG. 6 is a block diagram illustrating a generating circuit for a TGC control signal 120 according to a sixth embodiment. In FIG. 6, a charging and discharging current generator 300 is connected in series to a capacitance CCHG through a switch SWA, and the TGC control signal 120 is generated from the connecting point. The charging and discharging current generator 300 includes switches (SWA and SWB), a capacitance connection control signal 302, and a delay circuit 303, and the charging and discharging current generator 300 can connect or disconnect the capacitance CCHG to or from the wiring of the TGC control signal 120.

Ichg is an electric current source, and Vref is a power supply. The charging and discharging current generator 300 has a mode in which a constant current is carried to the capacitance CCHG using an MODECTL signal, and a mode in which the TGC control signal 120 is turned to a power supply potential or a ground potential. In the mode in which a constant current is carried to the capacitance CCHG, a timing signal 301 determines the timing of carrying the constant current to the capacitance CCHG. The electric current source Ichg can vary the constant current value.

In the mode in which a constant current is carried to the capacitance CCHG, the capacitance connection control signal 302 turns on the switch SWA and turns off the switch SWB to raise the timing signal 301 from TGC start time, and the electric current source Ichg is connected in series to carry the constant current to the capacitance CCHG from the TGC start time. Thus, the signal increasing with a lapse of time can be generated as the TGC control signal 120. The TGC control signal 120 is saturated at a power supply voltage at which the charging and discharging current generator 300 is operated, and the LNA has the maximum gain. In other words, this is TGC end time. In the case where reception is ended and the subsequent TGC operation is performed, electric charges in the capacitance CCHG is discharged. Discharging electric charges is performed in which the switch SWA is turned off using the delay circuit 303 by the capacitance connection control signal 302 to disconnect the electric current source Ichg from the capacitance CCHG, the switch SWB is then turned on, and the capacitance CCHG is connected in series to the ground potential. With this configuration, the path through which the discharge current carried can be limited to the loop near the capacitance CCHG.

In the case of the diagnostic mode using no time gain control TGC such as pulse doppler, the mode is switched to the mode in which the electric current output of the charging and discharging current generator 300 is turned off and the power supply potential or the ground potential is outputted as the TGC control signal 120.

Seventh Embodiment

Figure 7:
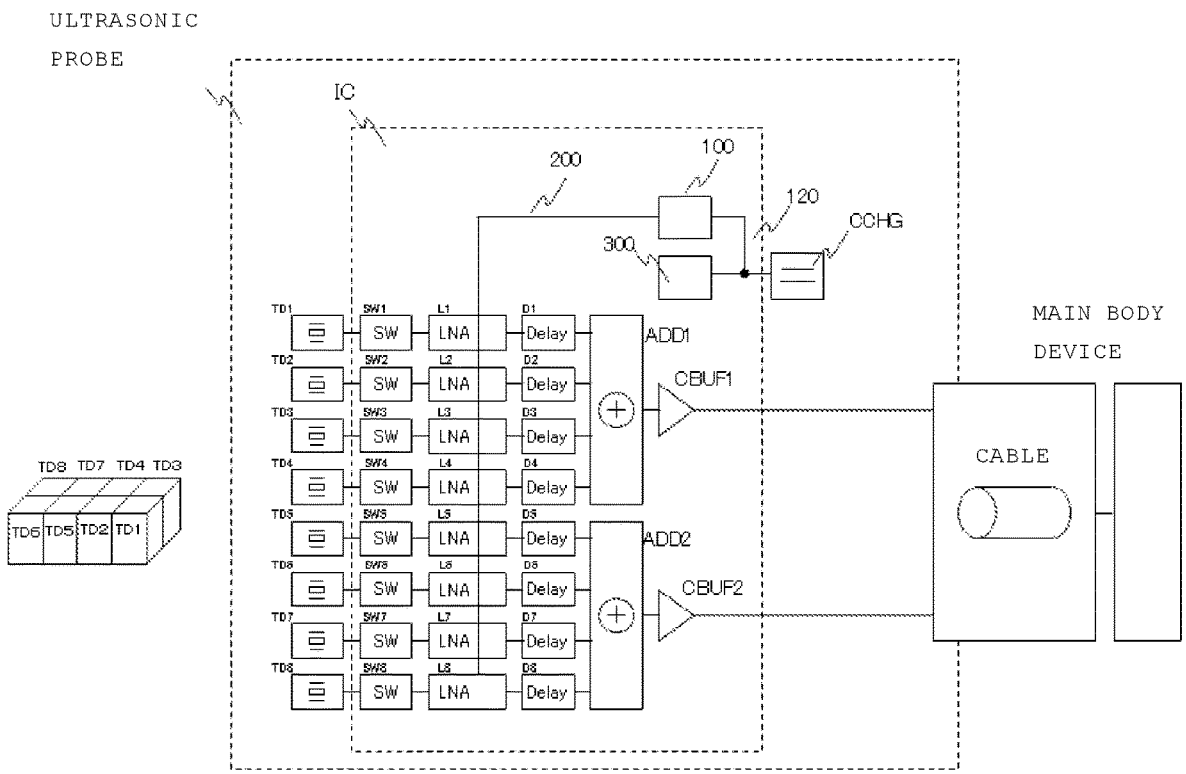
FIG. 7 is a block diagram of a first block in the case where a large number of the LNAs are mounted on a 2D array IC according to the seventh embodiment.

FIG. 7 is a block diagram of a first block according to a seventh embodiment in the case where a large number of the LNAs described in the first to five embodiments are mounted on a 2D array IC. In FIG. 7, components similar to components in FIGS. 1, 2, and 6 are designated with the same reference signs, and the description is omitted.

In FIG. 7, the IC is a 2D array IC, the ultrasonic probe is the 2D array ultrasonic probe, TD1 to TD8 are transducers, SW1 to SW8 are transmission/reception selector switches, L1 to L8 are LNAs, D1 to D8 are delay circuits, ADD1 and ADD2 are adding circuits, CBUF1 and CBUF2 are buffer circuits, and the ultrasonic probe further includes a cable and a main body device.

In FIG. 7, in the 2D array ultrasonic probe, the transducers are disposed in a matrix configuration like the transducers TD1 to TD8 shown on the left side. In in FIG. 7, four transducers are arranged in the long axis direction, two transducers are arranged in the short axis direction, and eight transducers are arranged. To the transducers TD1 to TD8, independent transmitter-receiver circuits mounted on the 2D array IC individually correspond at every path.

In in FIG. 7, a transmitting circuit, not shown, the transmission/reception selector switch SW, the LNA, and the delay circuit D correspond to the independent transmitter-receiver circuit.

For example, a signal converted from an ultrasonic wave to an electrical signal at the transducer TD1 is inputted to the LNA (L1) through the transmission/reception selector switch SW1 protecting the LNA from a signal with a large amplitude from the transmitting circuit, not shown, (since it is in reception time, the transmission/reception selector switch SW1 is turned on and connected at a low impedance). With the LNA (L1), the signal is amplified with no degradation of SNR as much as possible while saturation is avoided by the TGC scheme described in the first to five embodiments, and the signal is inputted to the delay circuit D1. The signal passes the delay circuit D1, and the signal is delayed for a desired period of time, and inputted to the adding circuit ADD1.

The signals converted from ultrasonic waves to electrical signals at the transducers TD2 to TD4 similarly individually pass the LNAs (L2 to 4) and the delay circuits D2 to D4, and inputted to the adding circuit ADD1. The adding circuit ADD1 adds these signals, the signals are amplified in electric power at the buffer circuit CBUF1 to drive the cable, and then transmitted to the main body device.

In transmission, the adding circuit ADD1, not shown, branches the same transmission signal to the delay circuits D1 to D4. The branched signals are delayed for a desired period of time at the delay circuits D1 to D4 to pass the transmitting circuit, not shown, and then drive the transducers TD1 to TD4 connected to the delay circuits D1 to D4. In transmission, the transmission/reception selector switch SW protecting the LNA (L) from a signal with a large amplitude from the transmitting circuit is turned off, and is connected to the LNA (L) at a high impedance. No switch is specifically provided between the transmitting circuit configured using a high withstand voltage transistor. The electrical signals by the transducers TD5 to TD8 are also similarly processed.

The delay time set at the delay circuits D1 to D8 is set such that the distance from a focal point to be a certain target, for example, to the center of the transducer group is calculated and the transmitter-receiver circuit disposed in the shortest distance transmits and receives signals at the latest time. That is, a pseudo-lens operation is performed using the 2D array IC.

Figure 8:
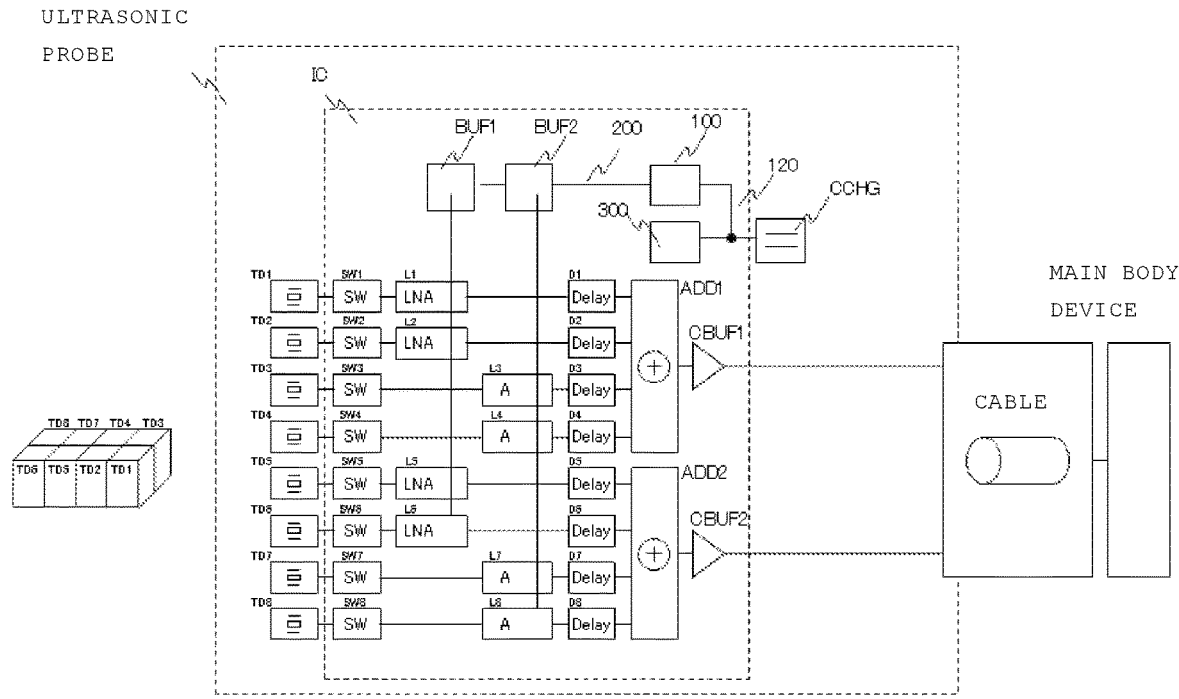
FIG. 8 is a block diagram of a second block in the case where a large number of the LNAs are mounted on a 2D array IC according to the seventh embodiment.

The TGC control signal 120 is a signal that is gradually increased from the time at which time gain control TGC is desired to start. The TGC control signal 120 is turned into a variable resistor control signal 200 by a TGC control circuit 100, and inputted to the arrow terminal of the variable resistor VR connected to the feedback unit of an amplifier circuit A in the LNA (L), and the TGC control signal 120 is shared by the transmitter-receiver circuits on eight paths. In other words, eight LNAs can be controlled by TGC control using one wiring. FIG. 8 shows a block diagram of a second block according to a seventh embodiment. In FIG. 8, BUF1 and BUF2 are buffer circuits. The TGC control signal 120 is turned into the variable resistor control signal 200 by the TGC control circuit 100, and inputted to the arrow terminal of the variable resistor VR connected to the feedback unit of the amplifier circuit A in the LNA (L). The variable resistor control signal 200 is buffered and connected to the LNAs (L1, L2, L5, and L6) by the buffer circuit BUF1 and buffered and connected to the LNAs (L3, L4, L7, and L8) by the buffer circuit BUF2. Thus, the buffer circuits BUF1 and BUF2 serve a function of reducing the influence of long-distance wiring.

In FIG. 8, wiring wired in the long axis direction of the transducer array on the left side are shared by the transmitter-receiver circuits on four paths. In FIG. 8, eight transducers are shown. For example, in the case where 64 LNAs are arranged on the long axis direction, 32 LNAs are arranged in the short axis direction, and 2048 LNAs in total are arranged for TGC control, 32 buffer circuits BUF are arranged following FIG. 8, and thus this enables TGC control of 2048 LNAs by one variable resistor control signal 200 only by sharing 64 differential voltages in the long axis direction.

As shown in the example in in FIG. 5, the buffer circuits BUF1 and BUF2 can be easily achieved in which MNT1 to MNT4 and MPT1 to MPT4 in the signal slope inverting circuit 121 are parallelized using a current mirror circuit, and their electric current outputs are inputted to a dummy circuit 110 for the LNA, an adding circuit 150, and a floating voltage circuit 130 separately individually provided.

Eighth Embodiment

Figure 9:
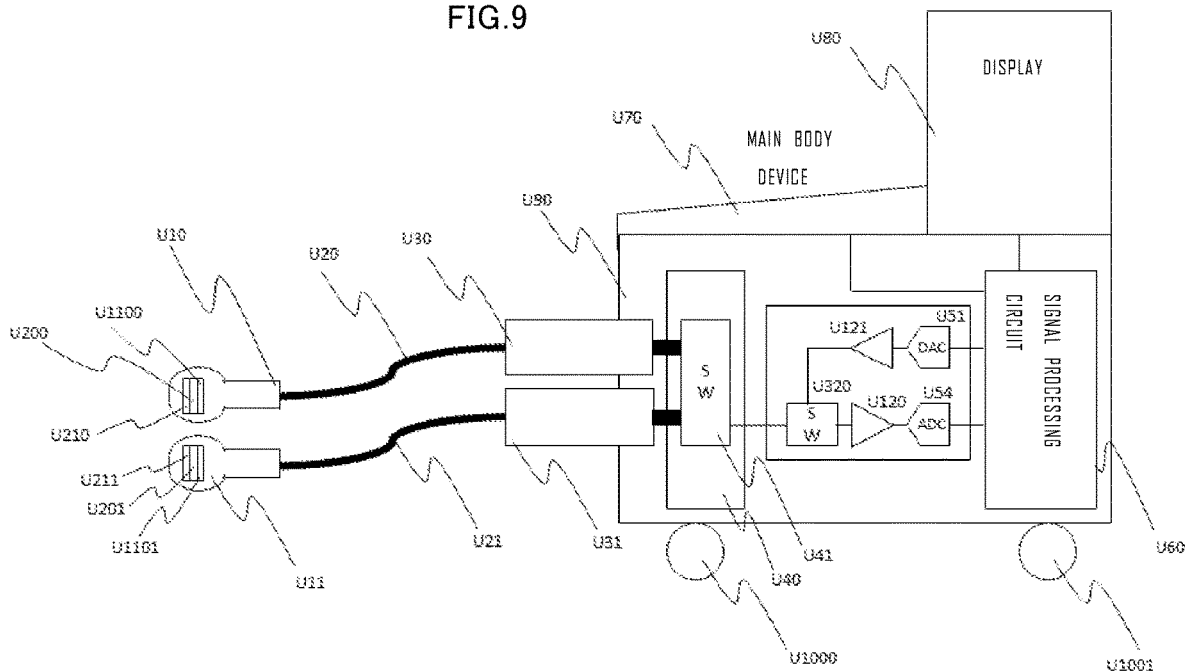
FIG. 9 is a block diagram of an ultrasonic diagnostic apparatus according to an eighth embodiment.

FIG. 9 is a block diagram of an ultrasonic diagnostic apparatus according to an eighth embodiment. In FIGS. 9, U10 and U11 denote 2D array ultrasonic probes, U20 and U21 denote cables, U30 and U31 denote connector boxes, U40 denotes a probe selector, U41 denotes a probe selector switch, U120 and U121 denote amplifiers, U51 denotes a digital analog converter, U320 denotes a transmission/reception selector switch, U54 denotes an analog digital converter, U60 denotes a signal processing circuit, U70 denotes an operation panel, U80 denotes a display, U90 denotes a main body device, U1100 and U1101 denote 2D array ICs, U200 and U201 denote matching layers, U210 and U211 denote acoustic lenses, and U1000 and U1001 denote casters.

The 2D array IC described so far, on which the TGC circuit is installed, corresponds to U1100 and U1101. The main body device U90 includes two connector boxes U30 and U31 to which two 2D array ultrasonic probes U10 and U11 are connected through the cables U20 and U21. However, the number is not limited to two. To the connector boxes U30 and U31, a conventional 1D array ultrasonic probe, for example, can also be connected. Some ultrasonic diagnostic apparatuses are provided with a terminal for connecting a connector box connecting a special ultrasonic probe exclusive for doppler. The main body device U90 is freely movable on the floor surface with the casters U1000 and U1001.

In regard to circuitry, the 2D array ultrasonic probe U10 and the 2D array ultrasonic probe U11 are switched for use using the probe selector U40 and the probe selector switch U41.

In the inside of the 2D array ultrasonic probes U10 and U11 the 2D array ICs (U1100 and U1101) are respectively built-in. on the surface of the 2D array IC (U1100), on which an external terminal connecting unit is mounted, a 2D array transducer, not shown, is connected. As described above, on the 2D array ultrasonic probe, a few thousands to ten thousand transducers are mounted in an array configuration. The 2D array transducer is mounted with a matching layer U200 that matches the 2D array transducer with the acoustic impedance of a living body such that efficient transmission and reception of ultrasonic waves is allowed and an acoustic lens U210 that converges ultrasonic beams. Similarly, the 2D array IC (U1101) is also mounted with the 2D array transducer, the matching layer U201, and the acoustic lens U211.

The amplifier U121 amplifies transmission signals, the transmission/reception selector switch U320 serves a function of preventing the sneak path of the transmission signal to the reception system, and the amplifier U120 amplifies reception signals. The signal processing circuit U60 is a logic circuit, receives the signal of the amplifier U120 as a digital signal through the analog digital converter U54 for signal processing. The signal processing circuit U60 inputs the signal after signal processing to the amplifier U121 through the digital analog converter U51, and transmits the signal to the 2D array ultrasonic probes U10 and U11 through the probe selector U40, the connector boxes U30 and U31, and the cables U20 and U21.

Various operations such as the observation of which side in a patient body are performed from the operation panel U70 of the main body device U90. The main body device U90 includes various diagnostic modes, and switching between diagnostic modes is also performed from the operation panel U70. Examples of diagnostic modes include Brightness (B), Pulsed Wave Doppler (PW), Color Flow Mapping (CFM), and Steerable CW Doppler (STCW) modes. The B mode is a mode in which the received amplitude strength of ultrasonic waves reflected off tissue is displayed corresponding to brightness, the PW mode is a mode in which ultrasonic waves are repeatedly transmitted to a certain depth and the frequency deviation of signals reflected from the site at every repeated transmission is measured to determine a blood flow velocity, and CFM is also referred to as color doppler, and is a mode in which the autocorrelation between reception signals at every transmission of ultrasonic waves is determined to visualize the blood flow velocity. The mode STOW is also a mode of measuring the blood flow velocity, and is suited to measuring fast blood flow velocities. The PW mode finds the blood flow velocity at a specific location, and can be displayed overlapping with B mode images. The CFM mode finds the mean velocity of locations at a large number of points on the received beams of ultrasonic waves, and the CFM mode is used for discovery of a backflow, for example.

The signal processing circuit U60 processes signals from the analog digital converter U54 to obtain diagnostic images in the various modes. The images are displayed on the display U80.

The TGC circuit according to the present embodiment can be used for receiving ultrasound signals in typical ultrasonic probes such as a 1D array IC, not limited to the 2D array IC. Equivalent TGC functions can be achieved by mounting the TGC circuit on the apparatus side, not on the ultrasonic probe.

As described above, the embodiments are described. The present invention is not limited to the forgoing embodiments, and includes various exemplary modifications. For example, the forgoing embodiments are described in detail for easily understanding the present invention, and the present invention is not necessarily limited to ones including all the configurations.

What is claimed is:

1. An ultrasonic probe transmitting an ultrasonic wave to a diagnostic organ and receiving a reception signal that is a reflected wave, the ultrasonic probe comprising:
a plurality of transducers;
a plurality of low-noise amplifier circuits individually corresponding to the plurality of transducers, wherein each of the plurality of low-noise amplifier circuits has
a variable resistor negative feedback unit making a resistance value variable by a voltage signal inputted to a control terminal of the variable resistor negative feedback unit; and
a control circuit,
wherein the control circuit includes:
a dummy circuit generating a bias voltage of the variable resistor negative feedback unit in each of the plurality of the low-noise amplifier circuits; and
an adding circuit outputting an added signal generated by adding the bias voltage from the dummy circuit and a control signal increasing or decreasing with a lapse of time, and wherein
each of the plurality of low-noise amplifier circuits input an output of the adding circuit to the control terminal of the variable resistor negative feedback unit to perform variable control on a gain of the low-noise amplifier circuit,
the control circuit further includes a floating voltage circuit,
the floating voltage circuit has a variable resistor making a resistance value variable by an electrical signal inputted to a control terminal,
the floating voltage circuit feeds a direct current signal to the control terminal of the variable resistor and carries a direct current to the variable resistor to generate a floating voltage, and
the control circuit inputs a signal that has been level shifted by the floating voltage based on the added signal output of the adding circuit to the control terminal of the variable resistor negative feedback unit in each of the plurality of low-noise amplifier circuits.

2. The ultrasonic probe according to claim 1, wherein the dummy circuit is composed of a dummy low-noise amplifier circuit and a dummy negative feedback resistor connected between an input and an output of the dummy low-noise amplifier circuit.

3. The ultrasonic probe according to claim 2, wherein the dummy circuit is mounted on a semiconductor die the same as the plurality of low-noise amplifier circuits.

4. The ultrasonic probe according to claim 1, wherein:
the variable resistor negative feedback unit is a first N-channel or a first P-channel field effect transistor, and the control terminal of the variable resistor negative feedback unit is a gate terminal of the first N-channel or the first P-channel field effect transistor;
the variable resistor of the floating voltage circuit is a second N-channel or a second P-channel field effect transistor having a gate connected to a drain, the direct current signal is fed to the second N-channel or the second P-channel field effect transistor, and a gate-to-source voltage of the second N-channel or the second P-channel field effect transistor is the floating voltage; and
the control circuit inputs the signal that has been level shifted by the floating voltage based on the added signal output of the adding circuit to the control terminal of the variable resistor negative feedback unit in each of the plurality of low-noise amplifier circuits.

5. The ultrasonic probe according to claim 4, wherein:
the low-noise amplifier circuit is an operational amplifier;
the first N-channel or the first P-channel field effect transistor is a variable resistor applying negative feedback from an output of the operational amplifier to an inverting input terminal; and
a non-inverting input terminal of the operational amplifier is supplied with a reference voltage.

6. The ultrasonic probe according to claim 1, wherein:
the low-noise amplifier circuit is a differential amplifier circuit having two field effect transistors arranged side by side; and
the variable resistor negative feedback unit is a third field effect transistor connected between sources of the two field effect transistors, and the variable resistor negative feedback unit inputs the output of the adding circuit to a gate of the third field effect transistor.

7. An ultrasonic probe transmitting an ultrasonic wave to a diagnostic organ and receiving a reception signal that is a reflected wave, the ultrasonic probe comprising:
a plurality of transducers;
a plurality of low-noise amplifier circuits individually corresponding to the plurality of transducers, wherein each of the plurality of low-noise amplifier circuits has a variable resistor negative feedback unit making a resistance value variable by a voltage signal inputted to a control terminal of the variable resistor negative feedback unit; and
a control circuit,
wherein the control circuit includes:
a dummy circuit generating a bias voltage of the variable resistor negative feedback unit in each of the plurality of the low-noise amplifier circuits; and
an adding circuit outputting an added signal generated by adding the bias voltage from the dummy circuit and a control signal increasing or decreasing with a lapse of time, and wherein
each of the plurality of low-noise amplifier circuits input an output of the adding circuit to the control terminal of the variable resistor negative feedback unit to perform variable control on a gain of the low-noise amplifier circuit,
the low-noise amplifier circuit is an inverter circuit having a first P-channel field effect transistor connected in series to a first N-channel field effect transistor,
the variable resistor negative feedback unit is a unit having a second N-channel field effect transistor connected in parallel to a second P-channel field effect transistor,
one end of the parallel connection of the second N-channel field effect transistor to the second P-channel field effect transistor is connected to a connecting point of the first P-channel field effect transistor to the first N-channel field effect transistor, and another end of the parallel connection is connected to gates of the first P-channel field effect transistor and the first N-channel field effect transistor,
a first added signal which is an output of the adding circuit outputting a sum of the bias voltage from the dummy circuit and a first control signal increasing or decreasing with a lapse of time and whose level is shifted by a gate-to-source voltage of a third N-channel field effect transistor is connected to a gate terminal of the second N-channel field effect transistor of the low-noise amplifier circuit,
a second added signal which is an output of the adding circuit outputting a sum of the bias voltage from the dummy circuit and a second control signal having a slope inverted to the first control signal with a lapse of time and whose level is shifted by a gate-to-source voltage of a third P-channel field effect transistor is connected to a gate terminal of the second P-channel field effect transistor of the low-noise amplifier circuit, and
by these connections, the gain of the low-noise amplifier circuit is variably controlled.

8. The ultrasonic probe according to claim 7, comprising:
a constant current generating circuit generating a signal increasing or decreasing with a lapse of time by charging a capacitance with a constant current; and
a single differential signal converter circuit receiving a difference between the signal and a reference direct current signal to generate the first control signal and second control signal.

9. The ultrasonic probe according to claim 8, wherein a gain of the single differential signal converter circuit is made variable to make the gain of the low-noise amplifier circuit variable.

10. The ultrasonic probe according to claim 8, wherein the reference direct current signal is made variable to make the gain of the low-noise amplifier circuit variable.

11. The ultrasonic probe according to claim 1, comprising a control signal generating circuit generating the control signal by charging a capacitance with a constant current.

12. The ultrasonic probe according to claim 11, wherein the control signal generating circuit includes a function of discharging the capacitance and/or a function of fixing the capacitance to a power supply voltage.

13. An ultrasonic diagnostic apparatus comprising:
the ultrasonic probe according to claim 1; and
a signal processing circuit obtaining information necessary for diagnosis based on a reception signal of the ultrasonic probe.

* * * * *